(12) United States Patent
Bernreuter

(10) Patent No.: US 9,364,176 B2
(45) Date of Patent: Jun. 14, 2016

(54) TISSUE OXIMETRY APPARATUS AND METHOD

(76) Inventor: Peter Bernreuter, Dettingen (DE)

(*) Notice: Subject to any disclaimer, the term of this patent is extended or adjusted under 35 U.S.C. 154(b) by 1031 days.

(21) Appl. No.: 13/283,044

(22) Filed: Oct. 27, 2011

(65) Prior Publication Data

US 2012/0190946 A1 Jul. 26, 2012

Related U.S. Application Data

(63) Continuation of application No. 11/780,997, filed on Jul. 20, 2007, now Pat. No. 8,055,321, which is a continuation-in-part of application No. 11/078,399, filed on Mar. 14, 2005, now Pat. No. 7,865,223.

(51) Int. Cl.
*A61B 5/1455* (2006.01)
*A61B 5/00* (2006.01)

(52) U.S. Cl.
CPC .......... *A61B 5/14552* (2013.01); *A61B 5/14551* (2013.01); *A61B 5/14553* (2013.01); *A61B 5/72* (2013.01); *A61B 2560/0238* (2013.01); *A61B 2562/0242* (2013.01)

(58) Field of Classification Search
CPC ............. A61B 5/1455; A61B 5/14551; A61B 5/14552; A61B 5/14553; A61B 5/72; A61B 5/7214; A61B 2560/0238; A61B 2562/0242
USPC ................................. 600/310, 322, 323, 336
See application file for complete search history.

(56) References Cited

U.S. PATENT DOCUMENTS

| | | |
|---|---|---|
| 2,706,927 A | 4/1955 | Wood |
| 2,790,438 A | 4/1957 | Taplin et al. |
| 3,412,729 A | 11/1968 | Smith, Jr. |
| 3,068,742 A | 8/1969 | Hicks, Jr. et al. |
| 3,461,856 A | 8/1969 | Polyani |
| 3,638,640 A | 2/1972 | Shaw |
| 3,704,706 A | 12/1972 | Herczfeld et al. |
| 3,709,612 A | 1/1973 | Clemens |
| 3,866,599 A | 2/1975 | Johnson |
| 3,998,550 A | 12/1976 | Konishi et al. |
| 4,014,321 A | 3/1977 | March |
| 4,029,085 A | 6/1977 | DeWitt et al. |
| 4,086,915 A | 5/1978 | Kofsky et al. |

(Continued)

FOREIGN PATENT DOCUMENTS

| | | |
|---|---|---|
| JP | 05212016 A | 8/1993 |
| JP | 630915 A | 2/1994 |

(Continued)

OTHER PUBLICATIONS

"U.S. Appl. No. 11/078,399, Examiner Interview Summary mailed Jun. 10, 2010", 3 pgs.

(Continued)

*Primary Examiner* — Eric Winakur
(74) *Attorney, Agent, or Firm* — Schwegman Lundberg & Woessner, P.A.

(57) ABSTRACT

An apparatus and method for determining tissue oxygenation such as arterial and venous oxygenation and cerebral oxygenation. In one embodiment, the optical properties of tissue are determined using measured light attenuations at a set of wavelengths. By choosing distinct wavelengths and using light attenuation information, the influence of variables such as light scattering, absorption and other optical tissue properties can be minimized.

24 Claims, 14 Drawing Sheets

(56) References Cited

U.S. PATENT DOCUMENTS

| | | |
|---|---|---|
| 4,119,406 A | 10/1978 | Clemens |
| 4,129,125 A | 12/1978 | Lester et al. |
| 4,167,331 A | 9/1979 | Nielsen |
| 4,222,389 A | 9/1980 | Rubens |
| 4,223,680 A | 9/1980 | Jobsis |
| 4,224,948 A | 9/1980 | Cramer et al. |
| 4,259,963 A | 4/1981 | Huch |
| 4,266,554 A | 5/1981 | Hamaguri |
| 4,281,645 A | 8/1981 | Jobsis |
| 4,321,930 A | 3/1982 | Jobsis et al. |
| 4,380,240 A | 4/1983 | Jobsis et al. |
| 4,416,285 A | 11/1983 | Shaw et al. |
| 4,447,884 A | 5/1984 | Wade |
| 4,452,250 A | 6/1984 | Chance et al. |
| 4,469,107 A | 9/1984 | Asmar et al. |
| 4,510,938 A | 4/1985 | Jobsis et al. |
| 4,576,173 A | 3/1986 | Parker et al. |
| 4,648,892 A | 3/1987 | Kittrell et al. |
| 4,655,225 A | 4/1987 | Dahne et al. |
| 4,700,708 A | 10/1987 | New, Jr. et al. |
| 4,714,341 A | 12/1987 | Hamaguri et al. |
| 4,738,267 A | 4/1988 | Lazorthes et al. |
| 4,773,422 A | 9/1988 | Isaacson et al. |
| 4,774,679 A | 9/1988 | Carlin |
| 4,800,495 A | 1/1989 | Smith |
| 4,800,885 A | 1/1989 | Johnson |
| 4,805,623 A | 2/1989 | Jobsis |
| 4,824,242 A | 4/1989 | Frick et al. |
| 4,836,207 A | 6/1989 | Bursell et al. |
| 4,840,485 A | 6/1989 | Gratton |
| 4,846,183 A | 7/1989 | Martin |
| 4,869,254 A | 9/1989 | Stone et al. |
| 4,880,304 A | 11/1989 | Jaeb et al. |
| 4,908,762 A | 3/1990 | Suzuki et al. |
| 4,926,867 A | 5/1990 | Kanda et al. |
| 4,942,877 A | 7/1990 | Sakai et al. |
| 4,972,331 A | 11/1990 | Chance |
| 5,032,024 A | 7/1991 | Cope |
| 5,035,243 A | 7/1991 | Muz |
| 5,057,695 A | 10/1991 | Hirao et al. |
| 5,058,588 A * | 10/1991 | Kaestle .................. 600/323 |
| 5,062,431 A | 11/1991 | Potter |
| 5,074,306 A | 12/1991 | Green |
| 5,088,493 A | 2/1992 | Giannini et al. |
| 5,090,415 A | 2/1992 | Yamashita et al. |
| 5,119,815 A | 6/1992 | Chance |
| 5,137,355 A | 8/1992 | Barbour et al. |
| 5,139,025 A | 8/1992 | Lewis et al. |
| 5,140,989 A | 8/1992 | Lewis et al. |
| 5,198,977 A | 3/1993 | Salb |
| 5,213,105 A | 5/1993 | Gratton et al. |
| 5,217,013 A | 6/1993 | Lewis et al. |
| 5,218,962 A | 6/1993 | Mannheimer et al. |
| 5,222,495 A | 6/1993 | Clarke et al. |
| 5,253,646 A | 10/1993 | Delpy et al. |
| 5,261,410 A | 11/1993 | Alfano et al. |
| 5,266,554 A | 11/1993 | Suchy et al. |
| 5,277,181 A | 1/1994 | Mendelson et al. |
| 5,285,783 A | 2/1994 | Secker |
| 5,318,023 A | 6/1994 | Vari et al. |
| 5,349,961 A | 9/1994 | Stoddart et al. |
| 5,385,143 A | 1/1995 | Aoyagi |
| 5,431,170 A | 7/1995 | Mathews |
| 5,465,714 A | 11/1995 | Scheuing |
| 5,477,853 A | 12/1995 | Farkas |
| 5,482,031 A | 1/1996 | Lambert |
| 5,482,034 A | 1/1996 | Lewis |
| 5,490,523 A | 2/1996 | Isaacson et al. |
| 5,497,769 A | 3/1996 | Gratton et al. |
| 5,524,617 A | 6/1996 | Mannheimer |
| 5,529,064 A | 6/1996 | Rall |
| 5,551,422 A | 9/1996 | Simonsen et al. |
| 5,551,423 A | 9/1996 | Sugiura |
| 5,584,269 A | 12/1996 | MacKenzie |
| 5,697,367 A | 12/1997 | Lewis et al. |
| 5,720,284 A | 2/1998 | Aoyagi et al. |
| 5,772,589 A | 6/1998 | Bernreuter |
| 5,779,631 A | 7/1998 | Chance |
| 5,792,052 A | 8/1998 | Isaacson |
| 5,795,292 A | 8/1998 | Lewis et al. |
| 5,800,349 A | 9/1998 | Isaacson et al. |
| 5,873,821 A | 2/1999 | Chance et al. |
| 5,879,294 A | 3/1999 | Anderson |
| 5,902,235 A | 5/1999 | Lewis et al. |
| 5,922,607 A | 7/1999 | Bernreuter |
| 6,226,540 B1 | 5/2001 | Bernreuter |
| 6,285,895 B1 | 9/2001 | Ristolainen et al. |
| 6,549,795 B1 | 4/2003 | Chance |
| 6,597,931 B1 | 7/2003 | Cheng et al. |
| 6,615,061 B1 | 9/2003 | Khalil et al. |
| 6,615,065 B1 | 9/2003 | Barrett et al. |
| 6,985,763 B2 | 1/2006 | Boas et al. |
| 7,047,054 B2 | 5/2006 | Benni |
| 7,072,701 B2 | 7/2006 | Chen et al. |
| 7,865,223 B1 | 1/2011 | Bernreuter |
| 8,055,321 B2 | 11/2011 | Bernreuter |
| 8,725,226 B2 | 5/2014 | Isaacson |
| 8,923,942 B2 | 12/2014 | Bernreuter |
| 2002/0058865 A1 | 5/2002 | Cheng |
| 2002/0082488 A1 | 6/2002 | Al-Ali et al. |
| 2002/0161290 A1 | 10/2002 | Chance |
| 2002/0198443 A1 | 12/2002 | Ting |
| 2003/0181798 A1 | 9/2003 | Al-Ali |
| 2004/0024297 A1 | 2/2004 | Chen et al. |
| 2005/0075549 A1 | 4/2005 | Kondoh |
| 2005/0228291 A1 | 10/2005 | Chance |
| 2006/0189862 A1 | 8/2006 | Casciani et al. |
| 2007/0055119 A1 | 3/2007 | Lash et al. |
| 2008/0015424 A1 | 1/2008 | Bernreuter |
| 2008/0058638 A1 | 3/2008 | Zhu et al. |
| 2008/0208011 A1 | 8/2008 | Shuler |
| 2009/0247853 A1 | 10/2009 | Debreczeny |
| 2009/0281403 A1 | 11/2009 | Benni |
| 2010/0094134 A1 | 4/2010 | Zhu et al. |
| 2010/0130840 A1 | 5/2010 | Isaacson |
| 2011/0060200 A1 | 3/2011 | Bernreuter |
| 2012/0184830 A1 | 7/2012 | Balberg et al. |
| 2014/0221798 A1 | 8/2014 | Isaacson |
| 2014/0249390 A1 | 9/2014 | Bernreuter et al. |

FOREIGN PATENT DOCUMENTS

| | | |
|---|---|---|
| JP | 630916 A | 2/1994 |
| JP | 08-271600 A | 10/1996 |
| JP | 11244268 A | 9/1999 |
| JP | 2004290412 A | 10/2004 |
| JP | 2005533609 A | 11/2005 |
| JP | 2005535359 A | 11/2005 |
| JP | 2008532680 A | 8/2008 |
| JP | 2010534083 A | 11/2010 |
| WO | WO-0181798 A1 | 11/2001 |
| WO | WO-2004010844 A2 | 2/2004 |
| WO | WO-2006094279 A1 | 9/2006 |
| WO | WO-2006124696 A1 | 11/2006 |
| WO | WO-2007012931 A2 | 2/2007 |
| WO | WO-2009013608 A2 | 1/2009 |
| WO | WO-2009013608 A3 | 1/2009 |
| WO | WO-2010056973 A1 | 5/2010 |

OTHER PUBLICATIONS

"U.S. Appl. No. 11/078,399, Final Office Action mailed Jun. 10, 2010", 12 pgs.

"U.S. Appl. No. 11/078,399, Non-Final Office Action mailed Dec. 3, 2009", 23 pgs.

"U.S. Appl. No. 11/078,399, Notice of Allowance mailed Sep. 1, 2010", 7 pgs.

"U.S. Appl. No. 11/078,399, Preliminary Amendment filed Jan. 7, 2009", 17 pgs.

"U.S. Appl. No. 11/078,399, Preliminary Amendment filed Mar. 10, 2006", 20 pgs.

"U.S. Appl. No. 11/078,399, Response filed Mar. 2, 2010 to Non Final Office Action mailed Dec. 3, 2009", 17 pgs.

(56) References Cited

OTHER PUBLICATIONS

"U.S. Appl. No. 11/078,399, Response filed Jul. 16, 2009 to Restriction Requirement mailed Jun. 16, 2009", 12 pgs.
"U.S. Appl. No. 11/078,399, Response filed Aug. 10, 2010 to Final Office Action maied Jun. 10, 2010", 14 pgs.
"U.S. Appl. No. 11/078,399, Restriction Requirement mailed Jun. 16, 2009", 7 pgs.
"U.S. Appl. No. 11/780,997, Examiner Interview Summary mailed May 26, 2011", 4 pgs.
"U.S. Appl. No. 11/780,997, Final Office Action mailed Mar. 2, 2010", 10 pgs.
"U.S. Appl. No. 11/780,997, Final Office Action mailed Apr. 8, 2011", 15 pgs.
"U.S. Appl. No. 11/780,997, Non-Final Office Action mailed Jun. 5, 2009", 19 pgs.
"U.S. Appl. No. 11/780,997, Non-Final Office Action mailed Jun. 11, 2010", 12 pgs.
"U.S. Appl. No. 11/780,997, Notice of Allowance mailed Jul. 12, 2011", 7 pgs.
"U.S. Appl. No. 11/780,997, Response filed Apr. 29, 2010 to Final Office Action mailed Mar. 2, 2010", 12 pgs.
"U.S. Appl. No. 11/780,997, Response filed Oct. 5, 2009 to Non Final Office Action mailed Jun. 5, 2009", 25 pgs.
"U.S. Appl. No. 11/780,997, Response filed Oct. 12, 2010 to Non-Final Office Action mailed Jun. 11, 2010", 15 pgs.
"U.S. Appl. No. 11/780,997, Response filed Jun. 8, 2011 to Final Office Action mailed Apr. 8, 2011", 15 pgs.
"U.S. Appl. No. 12/946,506, Preliminary Amendment mailed Jun. 23, 2011", 8 pgs.
"European Application Serial No. 06795079.0, Office Action mailed Aug. 1, 2011", 6 pgs.
"European Application Serial No. 06795079.0, Office Action mailed Sep. 25, 2009", 5 pgs.
"European Application Serial No. 06795079.0, Response filed May 25, 2010", 12 pgs.
"European Application Serial No. PCT/IB2006/001863, International Search Report and Written Opinion mailed Sep. 18, 2007", 13 pgs.
"International Application Serial No. PCT/IB2006/001863, International Preliminary Report on Patentability mailed Sep. 18, 2007", 13 pgs.
"International Application Serial No. PCT/IB2006/001863, International Search Report mailed May 23, 2007", 5 pgs.
"International Application Serial No. PCT/IB2006/001863, Written Opinion mailed Sep. 14, 2007", 12 pgs.
"International Application Serial No. PCT/IB2008/001932, International Search Report and Written Opinion dated Mar. 3, 2009", 13 pgs.
"International Application Serial No. PCT/US2009/064360, Search Report mailed Mar. 9, 2010", 7 pgs.
"International Application Serial No. PCT/US2009/064360, Written Opinion mailed Mar. 9, 2010", 6 pgs.
"Japanese Application Serial No. 2008-501451, Notice of Reason for Rejection mailed Oct. 21, 2011", 8 pgs.
Graaff, R., "Reduced Light-Scattering Properties for Mixtures of Spherical Particles: A Simple Approximation Derived from Mie Calculations", Applied Optics 31, (1992), 1370-1376.
Keogh, Brian F., "When Pulse Oximetry Monitoring of the Critically Ill is Not Enough", Anesth Analg 94, (2002), S96-S99.
Page, Andrew J, et al., "Distributed Monte Carlo Simulation of Light Transportation in Tissue", 4 pgs.
Rais-Bahrami, K, et al., "Validation of a noninvasive neonatal optical cerebral oximeter in veno-venous ECMO patients with a cephalad catheter", Journal of Perinatology, (2006), pp. 628-635.
Schmitt, Joseph M., "Simple Photon Diffusion Analysis of the Effects of Multiple Scattering on Pulse Oximetry", IEEE, vol. 38, No. 12, (Dec. 1991), 1194-1203.
"U.S. Appl. No. 12/946,506, Notice of Allowance mailed Mar. 14, 2014", 6 pgs.
"European Application Serial No. 06795079.0, Amendment filed Feb. 12, 2014", 20 pgs.
"European Application Serial No. 06795079.0, Amendment filed Dec. 7, 2007", 28 pgs.
"European Application Serial No. 06795079.0, Office Action mailed Mar. 27, 2014", 25 pgs.
"European Application Serial No. 06795079.0, Response filed Aug. 13, 2013 to Office Action mailed Apr. 11, 2013", 11 pgs.
"International Application Serial No. PCT/US2009/064360, Preliminary Report on Patentability mailed May 17, 2011", 7 pgs.
"Japanese Application Serial No. 2008-501451, Amendment filed Mar. 4, 2009", w/English claims, 15 pgs.
"Japanese Application Serial No. 2008-501451, Office Action mailed Jan. 24, 2014", English translation, 9 pgs.
"U.S. Appl. No. 12/618,120, Restriction Requirement mailed Jul. 26, 2012", 12 pgs.
"European Application Serial No. 06795079.0, Response filed May 16, 2012 to Office Action mailed Mar. 20, 2012", 12 pgs.
"Japanese Application Serial No. 2008-501451, Response filed Apr. 20, 2012 to Office Action mailed Oct. 21, 2011", 22 pgs.
"U.S. Appl. No. 12/618,120, Notice of Allowance mailed Sep. 3, 2013", 10 pgs.
"U.S. Appl. No. 12/618,120, Notice of Allowance mailed Dec. 24, 2013", 11 pgs.
"U.S. Appl. No. 12/618,120, Response filed Jul. 8, 2013 to Non Final Office Action mailed Jan. 7, 2013", 9 pgs.
"U.S. Appl. No. 12/946,506, Notice of Allowance mailed Aug. 20, 2013", 13 pgs.
"U.S. Appl. No. 12/946,506, Notice of Allowance mailed Dec. 6, 2013", 9 pgs.
"U.S. Appl. No. 12/946,506, Response filed Jun. 7, 2013 to Non Final Office Action mailed Jan. 7, 2013", 19 pgs.
"European Application Serial No. 06795079.0, Office Action mailed Apr. 11, 2013", 5 pgs.
"European Application Serial No. 06795079.0, Summons to Attend Oral Proceedings mailed Dec. 5, 2013", 5 pgs.
"Japanese Application Serial No. 2008-501451, Response filed Jul. 8, 2013 to Office Action mailed Feb. 8, 2013", w/English translation, 14 pgs.
"U.S. Appl. No. 12/618,120, Non Final Office Action mailed Jan. 7, 2013", 9 pgs.
"U.S. Appl. No. 12/618,120, Response filed Oct. 26, 2012 to Restriction Requirement mailed Jul. 26, 2012", 8 pgs.
"U.S. Appl. No. 12/946,506, Non Final Office Action mailed Jan. 7, 2013", 6 pgs.
"International Application Serial No. PCT/IB2008/001932, International Preliminary Report on Patentability mailed Feb. 4, 2010", 8 pgs.
"Japanese Application Serial No. 2008-501451, Office Action mailed Feb. 8, 2013", with English translation of claims, 7 pgs.
"U.S. Appl. No. 12/946,506, Notice of Allowance mailed Aug. 22, 2014", 7 pgs.
"U.S. Appl. No. 14/244,256, Non Final Office Action mailed Jan. 16, 2015", 6 pgs.
"Japanese Application Serial No. 2008-501451, Examiners Decision of Final Refusal mailed Sep. 9, 2014", 6 pgs.
U.S. Appl. No. 14/244,256, Final Office Action mailed Oct. 13, 2015, 6 pgs.
U.S. Appl. No. 14/244,256, Response filed Jul. 16, 2015 to Final Office Action mailed Jan. 16, 2015, 8 pgs.
Japanese Application Serial No. 2008-501451, Amendment and Argument filed on Jul. 24, 2014 in response to Office Action mailed Jan. 24, 2014, (w/ English Translation of Claims), 25 pgs.
Jacques, S.L., "Optical properties of biological tissues: a review", Phys. Med. Biol., 58, (2013), R37-R61.

* cited by examiner

TISSUE OXIMETRY APPARATUS AND METHOD

RELATED APPLICATIONS

This application is a continuation of U.S. patent application Ser. No. 11/780,997, filed on Jul. 20, 2007, which is a continuation-in-part of U.S. patent application Ser. No. 11/078,399 filed on Mar. 14, 2005, which applications are incorporated by reference herein in their entirety.

TECHNICAL FIELD

The present invention relates to a process and apparatus for improving accuracy of optical measurements of oxygenation of blood in tissue.

BACKGROUND OF THE INVENTION

A standard method to measure the arterial oxygenation of blood is known as pulse oximetry. Pulse oximeters function on the basis that at differing wavelengths, blood attenuates light very differently depending upon the level of oxygenation. Pulse waves starting from the heart cause in the arterial blood vessel system a periodic fluctuation in the arterial blood content in the tissue. As a consequence, a periodic change in the light absorption (FIG. 1) can be registered between the light transmitter, whose radiation passes through the tissue, and the receivers, which are integrated in a pulse oximetry sensor. The evaluation of the sensor signals is normally carried out at light wavelengths of w1=660 and w2=940 nm by calculating the differential change of light absorption. It is possible to create a measured variable R which is obtained in the following manner or in a similar manner:

$$R = Rw1, w2 = \frac{\Delta(LAw1) = \ln(I\max, w1) - \ln(I\min, w1)}{\Delta(LAw2)\ln(I\max, w2) - \ln(I\min, w2)} \quad \text{Eq: (1)}$$

The light intensities described in the formula represent the light intensities received in the receiver of the sensors used in pulse oximetry. The measured variable R serves as a measurement for the oxygen saturation. The formation of a quotient in order to form the measured variable is intended to compensate for any possible influences the haemoglobin content of the tissue, the pigmentation of the skin or the pilosity may have on the measurement of the oxygen saturation of arterial blood. The difference of the light attenuations at a minimum and maximum value is the delta of the light attenuations for each of both wavelengths.

Measuring oxygen saturation of arterial blood in the tissue in a range of 70 to 100% using light of wavelength 940 nm and 660 nm most often produces for one single application site sufficiently accurate measured values. However, in order to measure lower oxygen saturation of arterial blood it is necessary to assume a strong influence on the measured variable R in particular caused by perfusion (i.e. blood content) (see: IEEE; Photon Diffusion Analysis of the Effects of Multiple Scattering on Pulse Oximetry by J. M. Schmitt; 1991) and other optical parameters of tissue.

U.S. Pat. No. 5,529,064 to Rall, describes a fetal pulse oximetry sensor. For this kind of application, a higher measurement precision is desirable because a fetus has a physiological lower oxygenation than adult human beings and measurement error of SaO2 increases at low oxygenations.

U.S. Pat. No. 6,226,540 to Bernreuter, incorporated by reference herein, improves the precision of pulse oximetry. However, in order to measure on different body sites with the same high resolution for the arterial oxygenation, additional precision to measure optical tissue properties is necessary. Another problem is that pulse oximetry alone does not provide sufficient diagnostic information to monitor critically ill patients (See: When Pulse Oximetry Monitoring of the Critically Ill is Not Enough by Brian F. Keogh in Anesth Analg (2002), 94:96-99).

Because of this it would be highly desirable to be able to additionally measure the mixed venous oxygenation of blood SvO2. Methods to measure SvO2 with NIR were described by Jöbsis in U.S. Pat. No. 4,223,680 and by Hirano et al in U.S. Pat. No. 5,057,695. A problem of those disclosed solutions is that hair, dirt or other optically non-transparent material on the surface of tissue can influence the measured results for SvO2.

To measure the metabolism of blood oxygenation, Anderson et al in U.S. Pat. No. 5,879,294 disclose an instrument in which the second derivative of the light spectrum used delivers information about the oxygenation. Hereby, the influence of light scattering in tissue is minimized, which can result in higher measurement precision. A disadvantage of this solution is that the calibration of the optical instruments is complicated and expensive, which makes it impractical to use such devices for sports activity applications, where light weight wearable devices would be of interest. Similar problems are known for frequency domain spectroscopy disclosed for example in Gratton, U.S. Pat. No. 4,840,485. Oximetry devices, which are described in the present specification and which simply measure light attenuations of tissue at different wavelengths, are more feasible, flexible and reliable in practice than complex time resolved methods.

BRIEF SUMMARY OF THE INVENTION

The present invention is directed to an apparatus and method which eliminate influences on calibration by subtracting and adding measured light attenuations, and a model-based calibration calculation to improve precision of measured output variables. In one embodiment, an apparatus utilizes a combination of light emitters and detectors with a light wavelength combination of more than two wavelengths, where the peak spectrum of a third wavelength is about the geometric mean value of the first and second wavelengths.

As a result, influences on the calibration of different tissue properties can be minimized in order to measure arterial or venous or the combination of arterial and venous oxygenation. It has been discovered that by choosing one of the wavelengths as a geometric mean value of two other wavelengths, variations due to scattering can be reduced. Additional determination of light attenuation can reduce measurement errors because of variations of light absorption due to different tissue composition, i.e., variations of relative amounts of muscle, skin, fat, bone, etc.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

It is noted that as used in the present specification, "venous" and "mixed venous" may be synonyms, "attenuation" may refer to absolute or differential attenuation, "tissue oxygenation" may refer to arterial, mixed venous, or venous oxygenation or a combination of thereof, and the phrase "about" in reference to wavelengths may quantify in a band of +/−80 nm and in reference to distances quantifies in a band of +/−1 cm and that emitter corresponds to emitting point that means an area where light of at least one wavelength emitted by the sensor interface starts penetrating tissue, weighted values for light attenuations can have a value of one ore different values, the pulsatile part of a light attenuation corresponds to the AC signal of pulse oximetry and the non-pulsating part to the DC signal.

Figure 1:
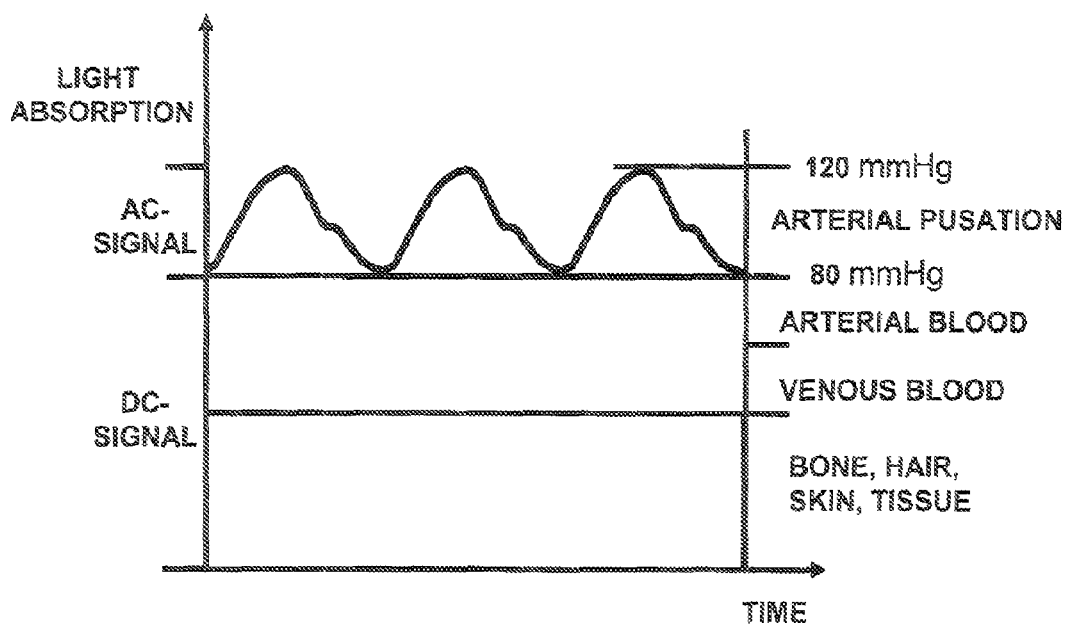
FIG. 1 is a graph showing changes of light absorption by blood over time.

The diagram of FIG. 1 shows the fundamental effect on which pulse oximetry and comparable methods to determine arterial blood oxygenation are based. When measuring light absorption of tissue in vivo light absorption changes synchronously with every heart cycle. The diagram illustrates the change of light absorption versus time, which is caused by arterial pulsations that can be measured while systole and diastole. During systole and diastole the pressure on the arterial vessel system varies from 80 mmHg to 120 mmHg. The change of light absorption is called the AC-signal. The DC-signal, the time-invariant part of light absorption, is caused by the non-pulsating part of the arterial blood, the venous blood, bone, hair, tissue and other constant absorbing constituents versus time. The time-invariant signal is the basis for the calculation of the mixed venous oxygenation of tissue; thus, a major part of the absorption is caused by venous blood and a minor part by arterial blood.

Figure 2:
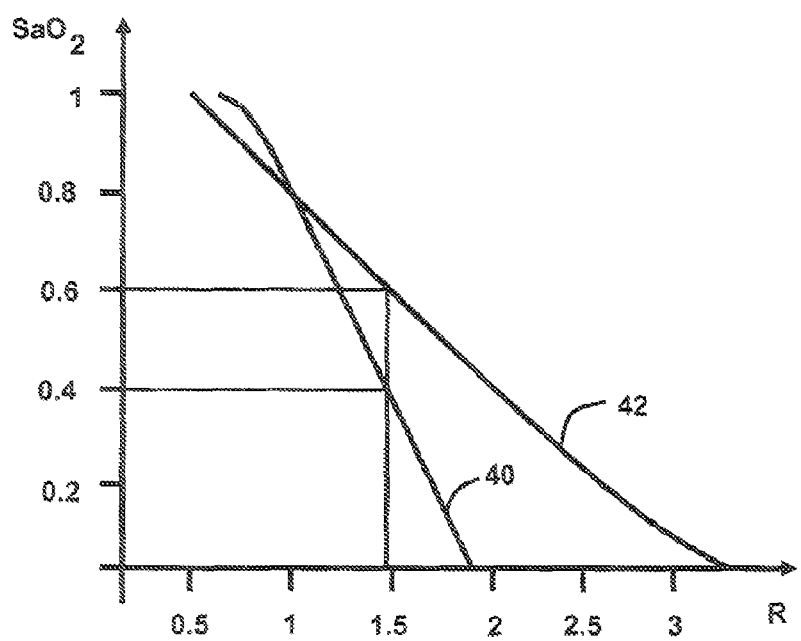
FIG. 2 is a graph illustrating the dependency of arterial oxygen saturation on the measurement variable R for different optical tissue properties.
Figure 6:
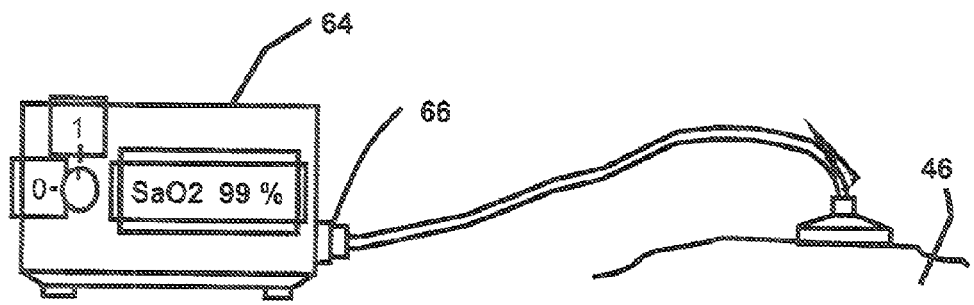
FIG. 6 is a schematic diagram of an oximetry system in operation.
Figure 18:
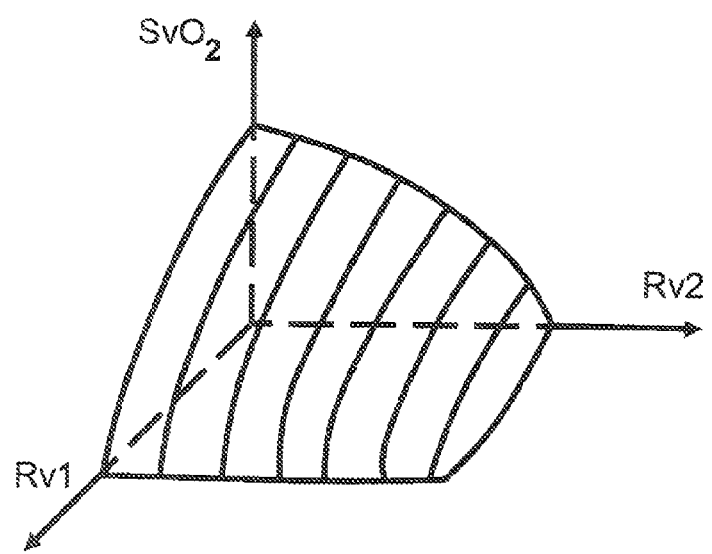
FIG. 18 is a diagram of a multidimensional calibration of oxygenation for the two measuring variables Rv1, Rv2 vs. SvO2.

FIG. 2 shows two calibration curves in a diagram with SaO2 vs. R. Calibration line 42 is only valid for a first distinct set of optical properties. Calibration line 40 is only valid for a second distinct set of optical properties. The valid set of optical properties can be determined by an optical system illustrated in FIGS. 3 and 6 with a sensor 31S, which is placed on tissue 46 and connected via a plug 66 to a display device 64. Additionally, FIG. 2 shows two horizontal lines at SaO2=0.6 and at SaO2=0.4 and one vertical line at R=1.4. If an optical system determines only R without registering the two different sets of optical properties, this would result in an error of 0.2 SaO2 (SaO2 at first set of optical properties–SaO2 at second set of optical properties). An analogous relation also exists for the mixed venous saturation of blood SvO2 and a measurement variable Rv1 and Rv2 for mixed venous oxygenation (FIG. 18).

Figure 3:
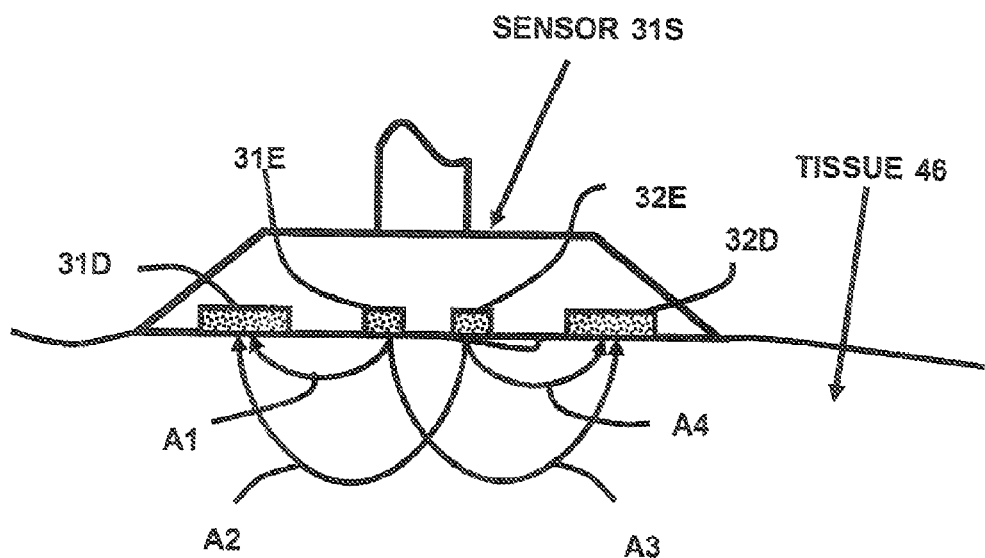
FIG. 3 shows a reflectance oximetry sensor according to the invention in schematic cross-section.

FIG. 3 shows an oximetry sensor 31S on the upper part of the figure which is placed on tissue 46. The sensor 31S contains two light emitters 31E, 32E and two light detectors 31D, 32D. The arrows A1 through A4 show how light passes from emitters to detectors through tissue. A1 stands representative for light which is emitted in emitter 31E and received in detector 31D. A2 is light emitted in emitter 32E and detected in detector 31D. A3 is light emitted in 31E and received in 32D and A4 is light emitted in emitter 32E and detected in detector 32D.

Figure 4:
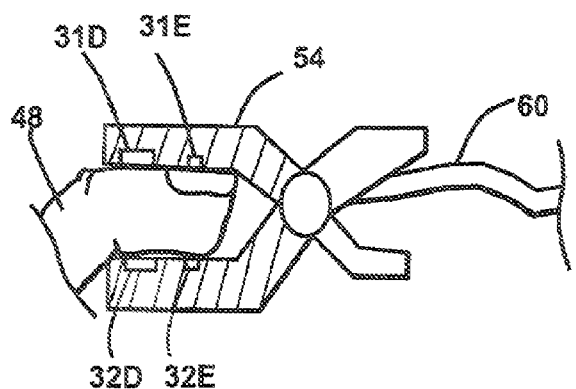
FIG. 4 shows a finger clip sensor according to the invention in schematic cross-section.

FIG. 4 shows a finger clip sensor 54 which is fixed on a finger 48. The finger clip sensor incorporates emitters 31E, 32E and detectors 31D, 32D. The electrical sensor signals of the finger clip sensor are transmitted via a sensor cable 60. The signals can also be conveniently transmitted wirelessly by means well known in the art (not shown).

Figure 5:
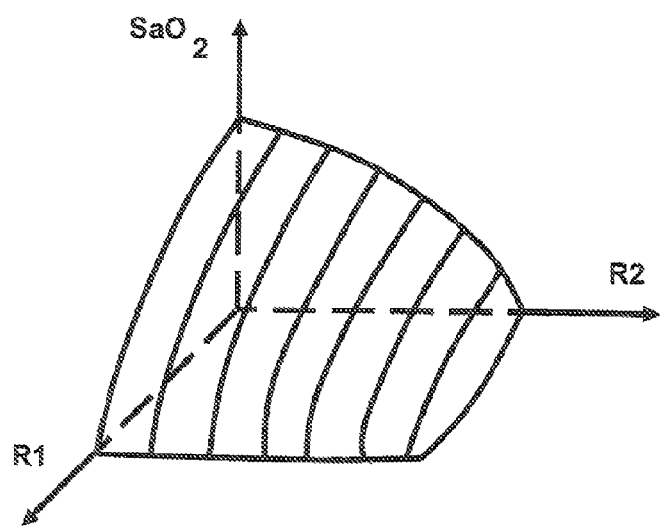
FIG. 5 is a diagram of a multidimensional calibration of oxygenation for the two measuring variables R1, R2 vs. SaO2.

FIG. 5 illustrates a multidimensional calibration of SaO2 vs. R1 and R2. A certain combination of R1 and R2 corresponds to a data point on the calibration plane, which indicates the saturation level SaO2. An analogous relation also exists in FIG. 18 for the mixed venous saturation of blood SvO2 and two related measurement variables Rv1 and Rv2 for mixed venous oxygenation.

Figure 7:
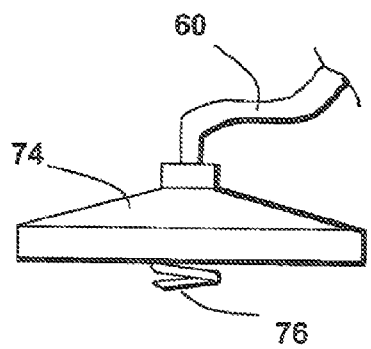
FIG. 7 is a side view of a fetal scalp sensor according to the invention.
Figure 8:
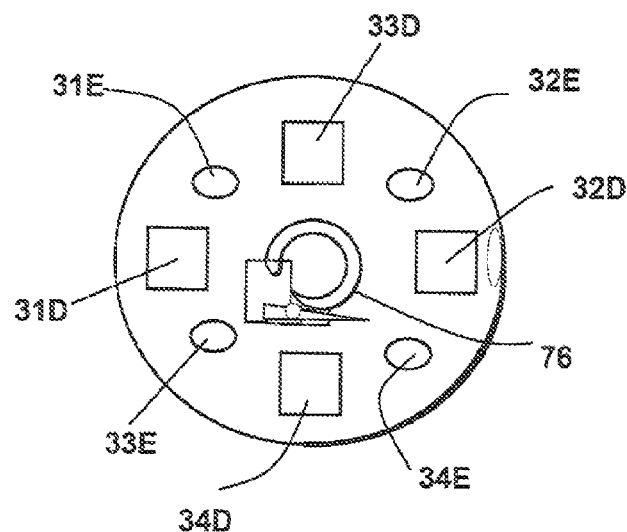
FIG. 8 is a bottom view of the sensor of FIG. 7.

FIGS. 7 and 8 show a fetal scalp sensor 74 with a set of emitters 31E, 32E, 33E and 34E and a set of detectors 31D, 32D, 33D and 34D from side and bottom views, respectively. The sensor can be fixed on the scalp of the fetus via a spiral needle 76 during labor. Additionally, an electrocardiogram (ECG) of the fetus can be transmitted via the needle 76.

Figure 9:
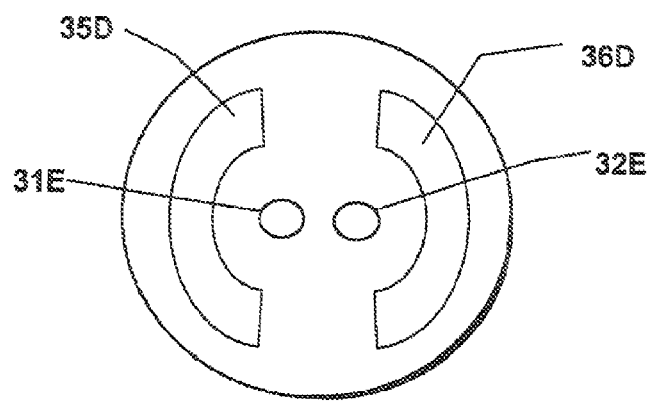
FIG. 9 is a bottom view of the sensor of FIG. 3.

FIG. 9 is a bottom view of sensor 31S from FIG. 3. Detectors 35D and 36D have a concentric form to maximize reception of light emitted by the emitters 31E and 32E.

Figure 10:
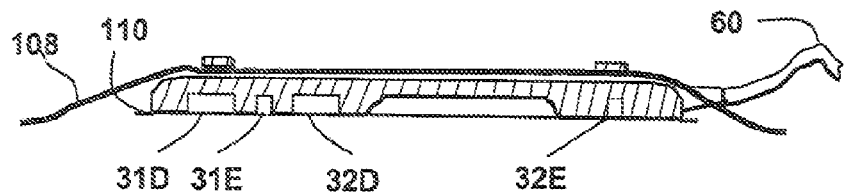
FIG. 10 is a side cross-sectional view of a variation of the sensor of FIG. 3.
Figure 11:
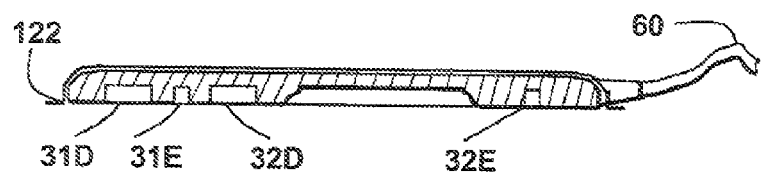
FIG. 11 is a side cross-sectional view of another variation of the sensor of FIG. 3.
Figure 12:
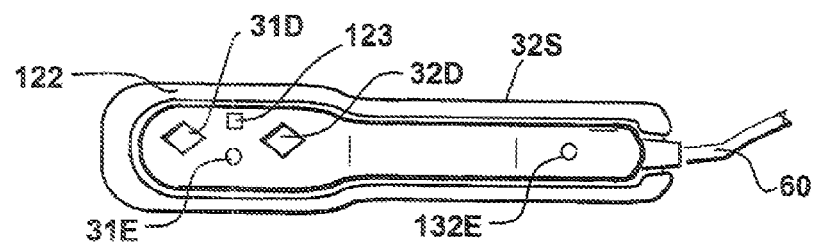
FIG. 12, FIG. 12A-12D is a bottom view of the sensor of FIG. 11 and several variations of emitter detector position on sensor interface.

FIGS. 10-12 show several modifications of sensor 31S. FIG. 10 shows sensor in side view with a flat body where detectors 31D, 32D and the emitter 32E are grouped close together and emitter 32E is positioned far from this group. The sensor can be fixed via a band 108 on tissue. A light shield 110 minimizes the influence of ambient light.

FIG. 11 shows a sensor with a sensor holder 122.

Figure 12A:
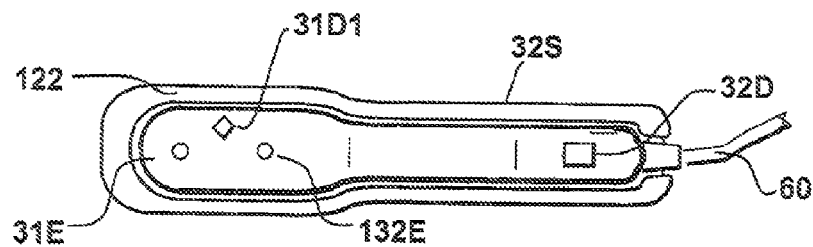
Figure 12B:
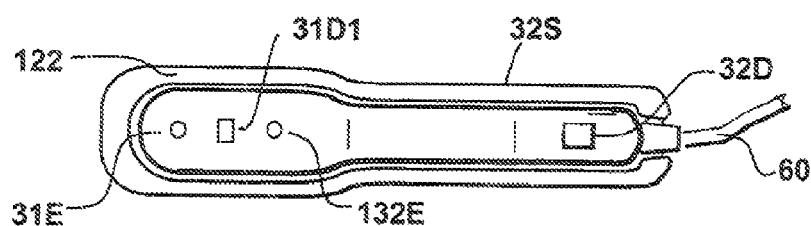
Figure 12C:
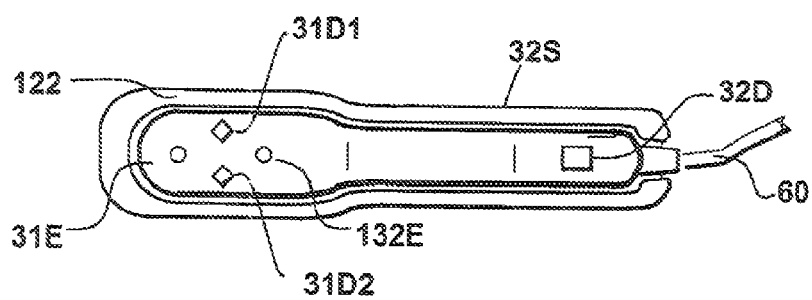
Figure 12D:
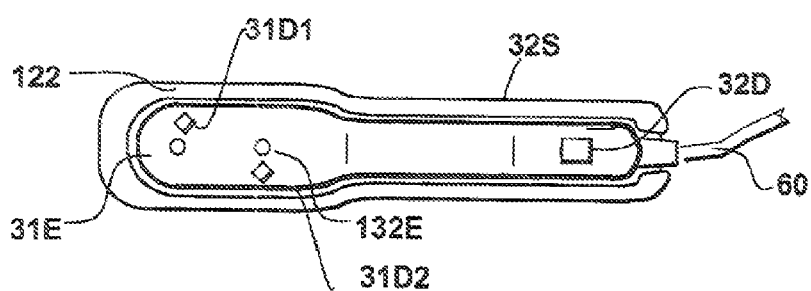

FIG. 12 is a bottom view of sensor of FIG. 11. The bottom side of sensor holder 122 can be covered with medical glue or adhesive. If sensor holder 122 is placed on sensor 31S according to FIG. 11 and applied to tissue 46, fixation is possible by glue on sensor holder 122. Sensor holder 122 can be constructed as inexpensive and disposable. Alternatively, the bottom side of the sensor, which is applied to tissue, can be directly covered with glue. The disadvantage of this is that the sensor can not be reused. The heart rate is detected via ECG-electrode 123 which contacts the skin FIG. 12 A shows a sensor where the emitters 31E and 132E are placed close and a first detector 31D1 is positioned near and a second 32D is positioned far towards the emitters. FIG. 12B is a slight modification of FIG. 12B showing a sensor where detector 31D1 is positioned in one line with the emitters 31E and 132E. In FIG. 12C instead of detector 31D1 two detectors 31D1 and 31D2 are illustrated. FIG. 12D is a modification of FIG. 12C showing that detectors 31D1 and 31D2 can be placed in various topologies on the sensor interface—here close to the emitters 31E and 132E.

Figure 13A:
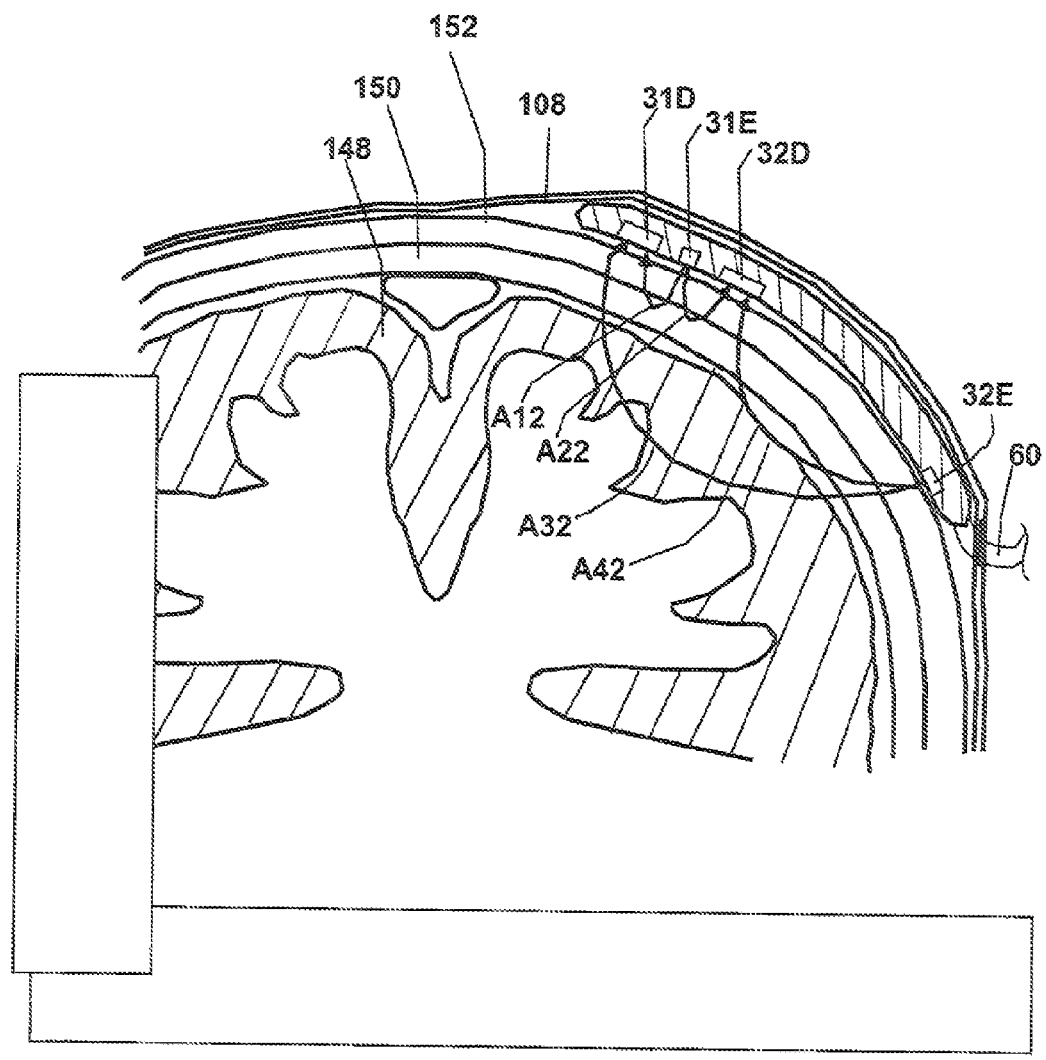
FIGS. 13A, 13B and 14 are side cross-sectional views of reflectance sensors fixed on the forehead.
Figure 13B:
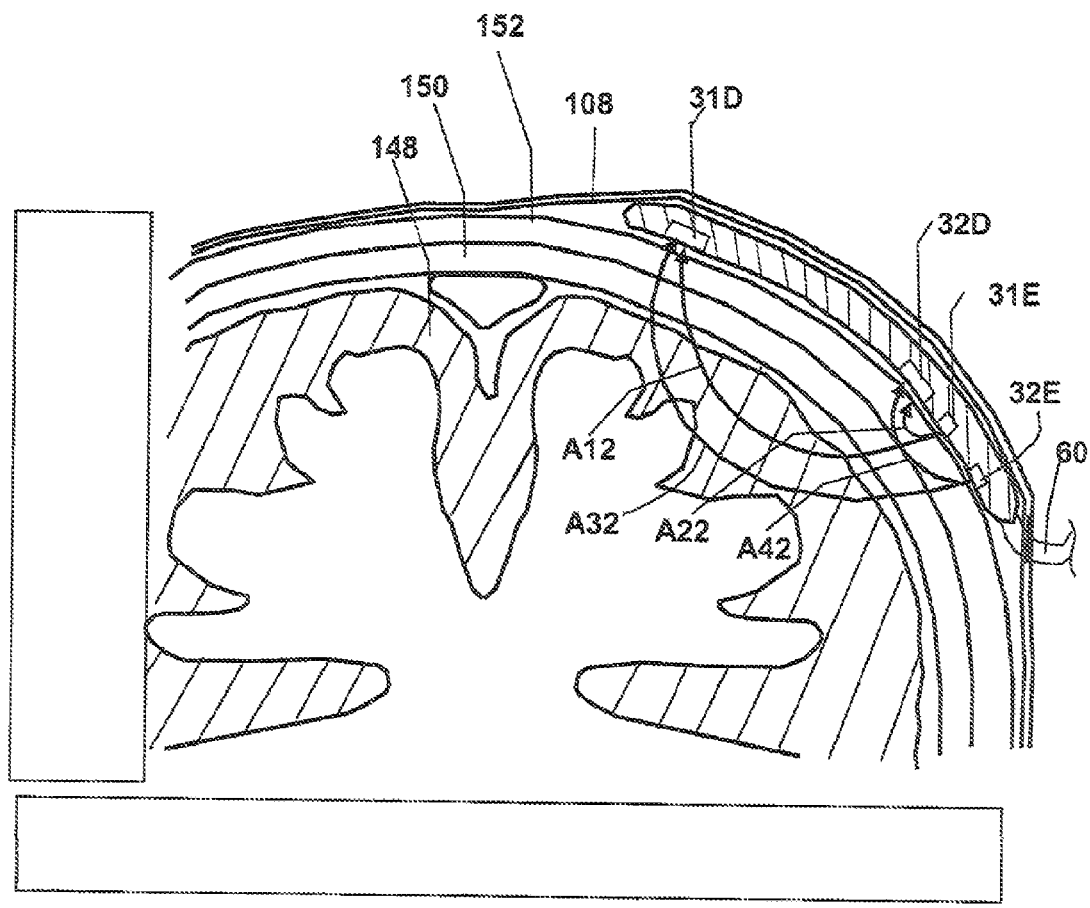
Figure 14:
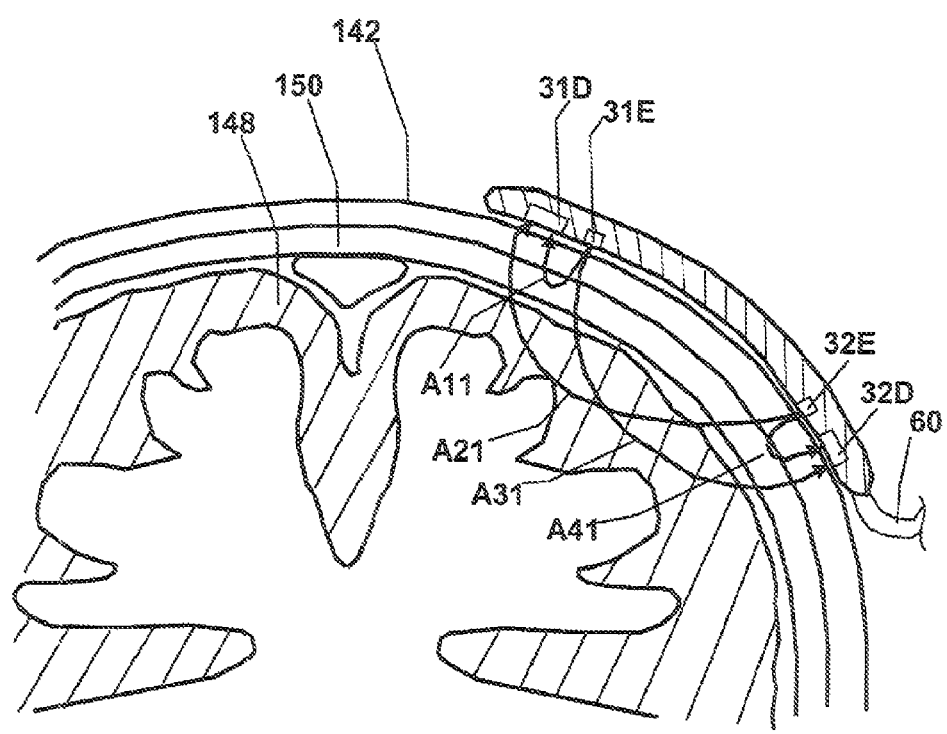

FIGS. 13A, 13B and 14 show variations of sensor 32S applied on the forehead of a person. In the first variation shown in FIGS. 13A and 13B, sensor 32S is fixed via a band 108 to the forehead. The arrows A32 and A42, which represent how light travels from the emitters 31E, 32E to the detectors 31 and 32D, pass through forehead tissue 152 and bone of skull 150 and pass or touch brain 148. The arrows A12 and A22 only pass through forehead tissue 152 and bone of skull 150. A difference of FIG. 13A and FIG. 13B is that in FIG. 13A the detectors 31D and 32D are positioned in close proximity whereas in FIG. 13B the emitters are placed in close proximity.

The second variation of sensor 32S also applied on the forehead is shown in FIG. 14. The arrows A11, A21, A31 and A41 compared with arrows A12, A22, A32 and A42 of FIGS. 13A and 13B show that by variation of the position of light detectors and emitters, oxygen content can be sensed differently without changing the outline of the sensor variation used.

Figure 15:
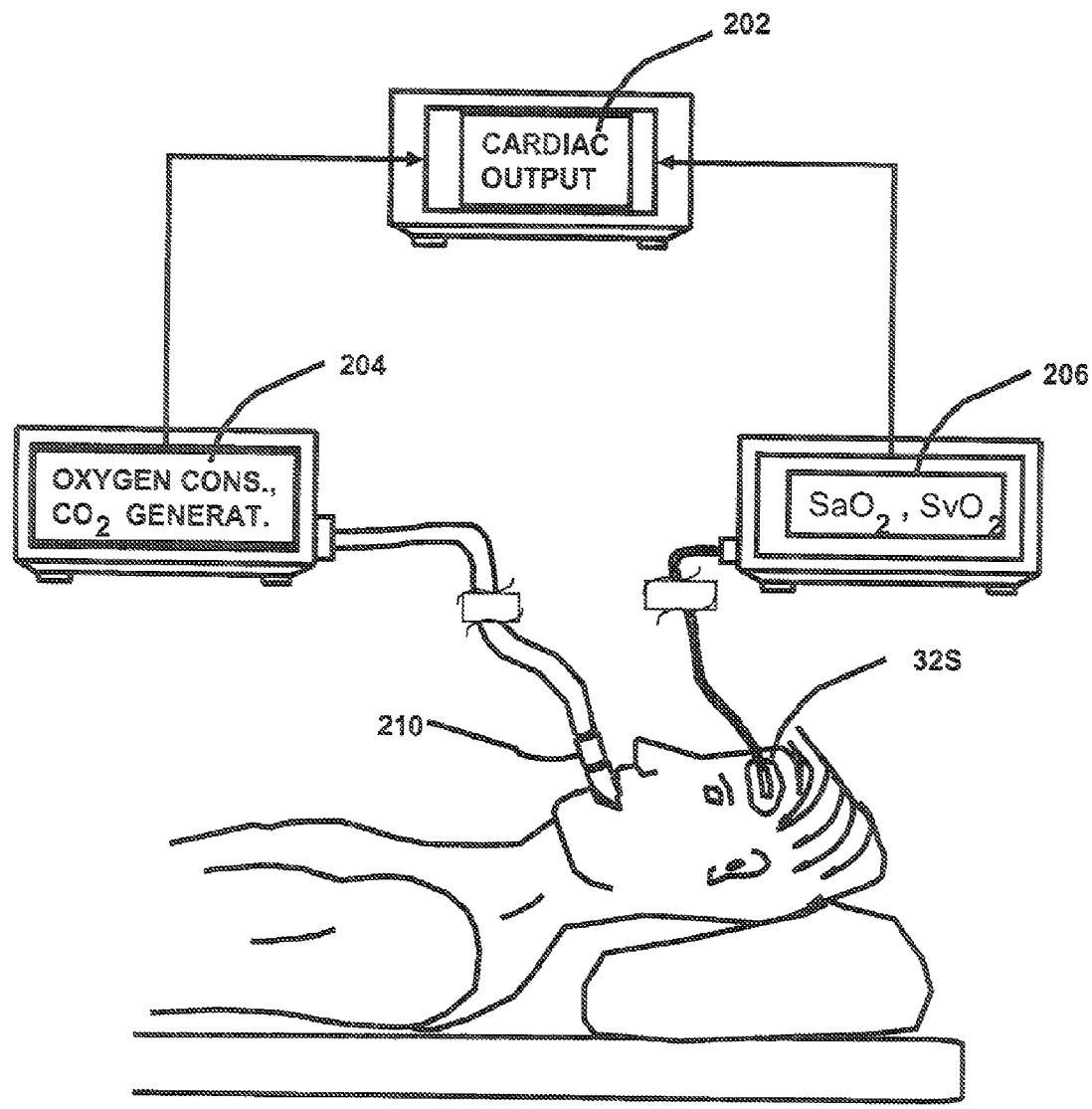
FIG. 15 shows a system for determining cardiac output.

FIG. 15 shows a patient lying on a bed being supplied with oxygen by an intubation tube 210, and an anesthesia machine 204. The anesthesia machine 204 is connected to the patient and has an inventive device for measuring oxygen consumption or carbon dioxide production of the patient. The sensor 32S is placed on the forehead of the patient, and is connected with oxygen extraction monitoring device 206, which calculates SaO2 and SvO2 and oxygen extraction. The monitoring device 206 and the anesthesia machine 204 are linked to a third device 202, which calculates cardiac output or trend of cardiac output.

Figure 16:
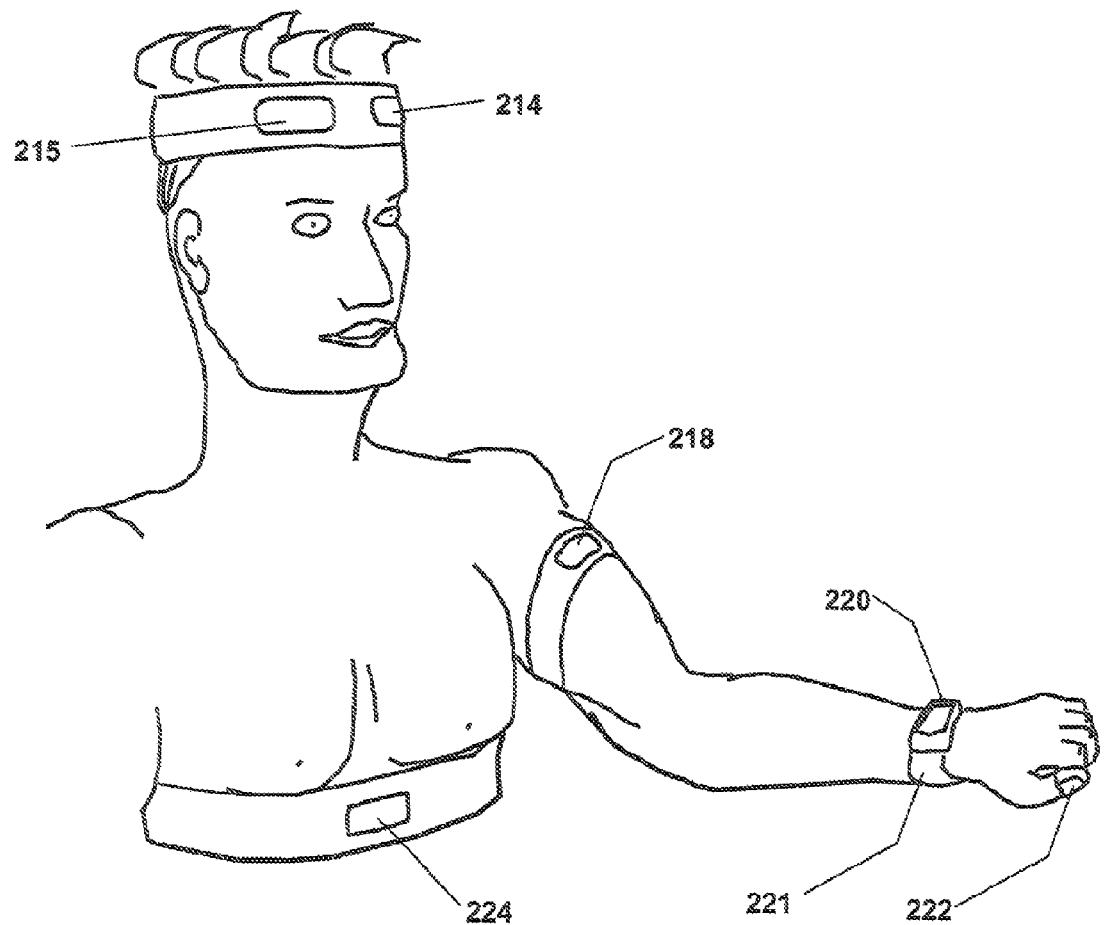
FIG. 16 shows person with wrist worn display and sensor interface with sensor applications on different sites of the body, two sensor interfaces for each hemisphere of brain placed on the forehead.

FIG. 16 illustrates the use of oxygen monitoring at different application sites e.g. for sports activity or other medical applications, in which a wrist worn display device 220 can receive oxygenation data from a forehead-band-sensor with sensor interfaces 214 and 215 for both hemispheres of brain, from a chest-band-sensor 224, from an arm-band-sensor 218 or a special variation of this the wrist band with sensor interface 221 or from a finger-glove-sensor 222.

Figure 17A:
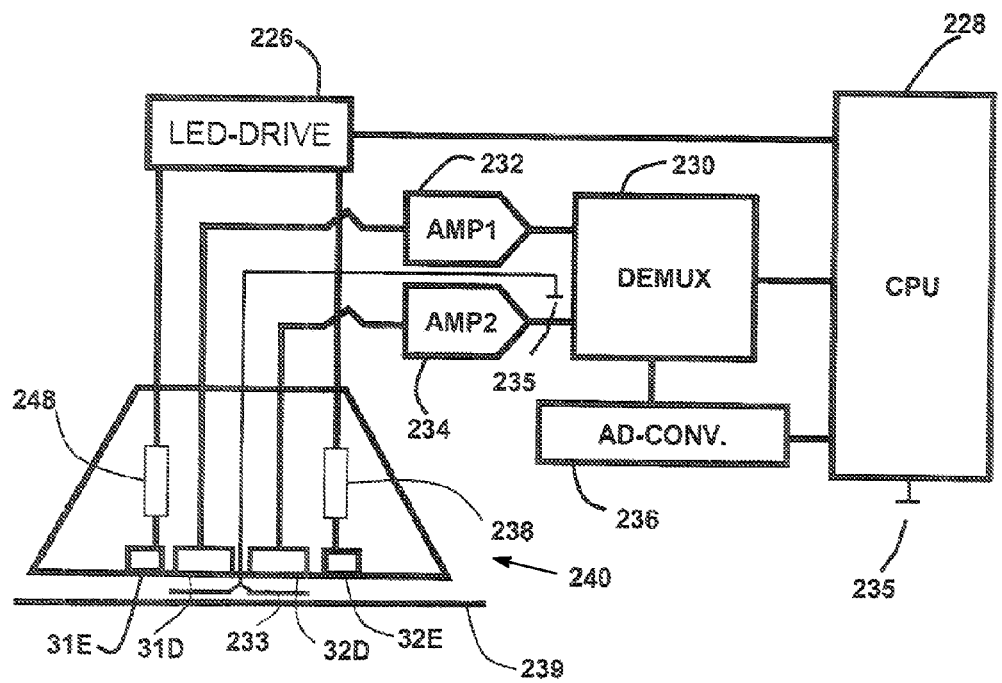
FIG. 17A is a schematic diagram of a hardware processing unit for an oximetry system according to the invention with detector ground shield and elastic isolating layer towards tissue, and FIG. 17B includes a side view of a sensor part.
Figure 17B:
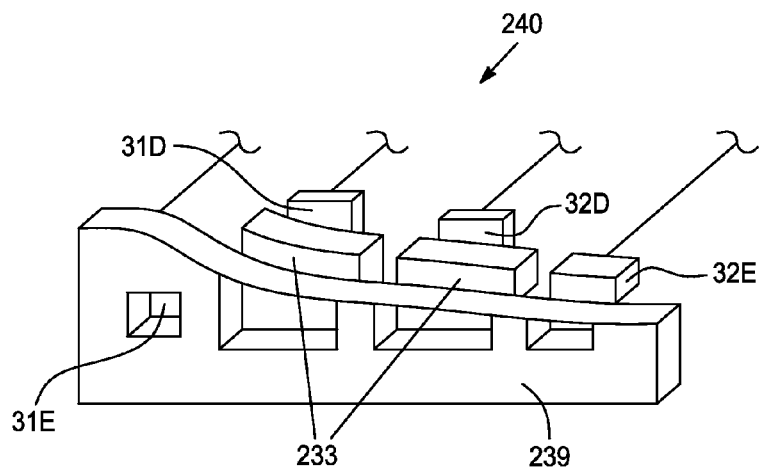

FIG. 17a shows the hardware for evaluating oxygenation by using two emitters 31E and 32E and two detectors 31D and 32D. The LED-drive 226 energizes the two emitters via lines 238, 248 which can incorporate coding hardware, to adjust calibration for the multidimensional calibration or to adjust calibration for varying emitter detector geometry. The amplifiers AMP1 232 and AMP2 234 are connected to detectors 31D and 32D. The demultiplexer DEMUX 230 selects each wavelength used in every emitter timed synchronously according to the switching state of the LED-DRIVE 226 and delivers the measured data via an AD-Converter AD-CONV 236 to the CPU 228. The sensor interfaces comprises an isolating layer 239 towards the patient which may consist of elastic material. The light detectors 31D and 32D are shielded with a grounded layer 233 which is connected to a ground line 235. The ground shield can consist for example of an electrical conductive layer or metallic grid. FIG. 17b depicts a cross-sectional view of sensor 240.

Figure 19:
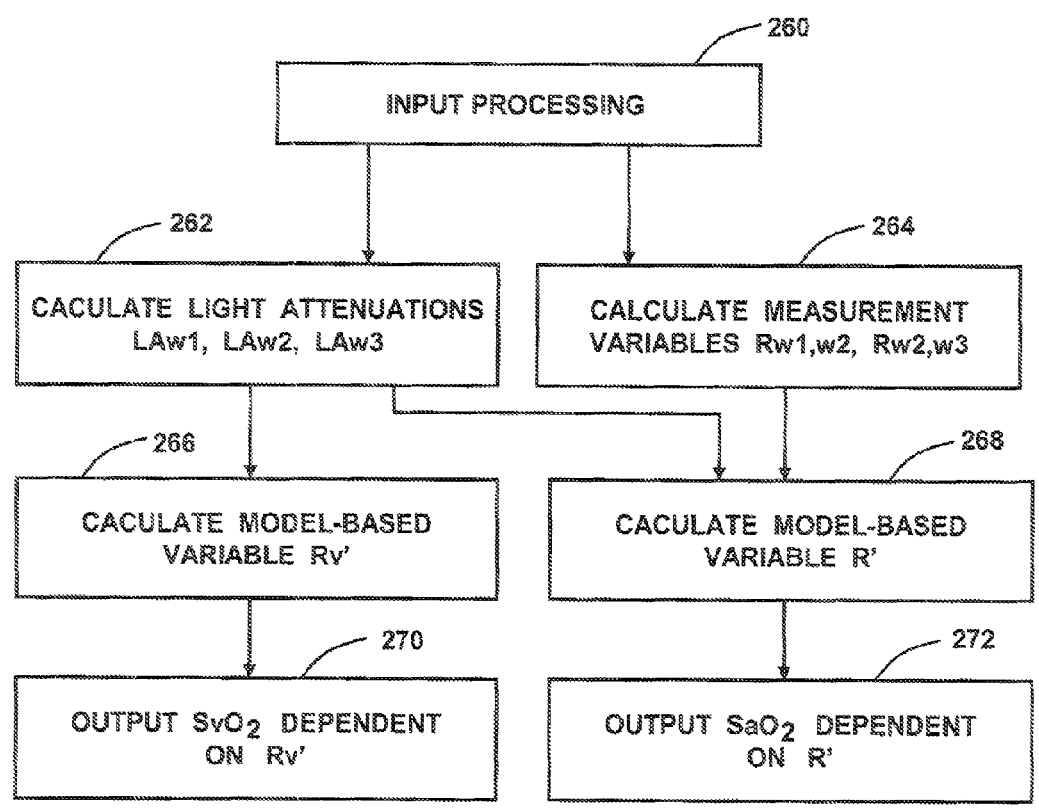
FIG. 19 is a flow chart illustrating signal processing flow for a model-based determination of oxygen in blood.

FIG. 19 illustrates the signal flow of a model-based calibration. An input processing circuit 260 is the first part of the signal flow. The processing circuit is connected with a circuit for calculating light attenuations 262 and a circuit calculating different measurement variables 264. The calculation for light attenuations 262 is a basis for a model-based determination circuit for mixed venous oxygenation 266 with a joint circuit to output a value for the mixed venous oxygenation SvO2 270. A model-based determination circuit for arterial oxygenation 268 is connected to the circuit for calculating light attenuations 262 and the circuit calculating different measurement variables 264. The output value for a arterial oxygenation circuit for SaO2 272 is linked to the model-based calculation for SaO2 268.

By using three instead of two wavelengths to measure the arterial oxygenation, the following approximation can be derived with the help of diffusion theory. The result of this operation is:

$$R' = \frac{Rw2, w1 * LAw2 * LAw0 + Q}{Rw1, w0 LAw1 * LAw1} \quad \text{eq. (2)}$$

where Rw2,w1 and Rw1,w0 are calculated according to equation (1) using wavelengths w0, w1, and w2 and Q is a correction parameter.

Light attenuation LAwx can be calculated in the following or similar manner:

$$LAwx = \ln(Iwx/Iwxo) \quad \text{eq. (3)}$$

LAwx corresponds to the logarithm of the ratio of light intensity Iwxo which is the emitted and light intensity Iwx the received light passing through tissue at wavelength wx. The index following suffix wx indicates the selected wavelength. Graaff et al showed that scattering in tissue decreases for higher wavelengths according to exponential functions (see: Applied Optics; Reduced Light-Scattering Properties for Mixtures of Spherical Particles: A Simple Approximation Derived from Mie Calculations by R. Graaff; 1992).

Absorption variation may also be taken from other measures or approximations such as the ac/dc ratio. The amplitude may be any measure such as peak-to-peak, RMS, average, or cross correlation coefficient. It may also be derived from other techniques such as Kalman filtering or a measure of the time derivative of the signal. Also, while calculations utilizing ratios of absorptions at different wavelengths are shown, alternate calculations may be used to give the same or approximately the same results. For instance the absorptions could be used directly, without calculating the ratios.

A preferred selection of the wavelengths combination to reduce the influence of scattering is defined by the following equation, with wavelength w1 as the geometrical mean value of wavelength w0 and wavelength w2, defined as:

$$w1 = SQRT(w0*w2) \qquad \text{eq. (4)}$$

This combination minimizes the variation band of correction parameter Q, which has a default value of about one. The measurement variable R' of equation (2) has minimized error related to variation of scattering and blood content of tissue.

Example 1

The sensor 31S shown in FIG. 3 is used to determine the arterial oxygenation and the mixed venous blood oxygenation of tissue with improved precision. Equation (2) is used to provide a measurement variable R' for the arterial oxygenation. For each of the emitters 31E and 32E, three wavelengths are defined. Initially, two measurement wavelengths w0=940 nm and w2=660 nm are selected. Using equation (4) the third wavelengths w1 is about 788 nm. Wavelength w1=805 nm is chosen because it is close to the calculated third wavelength and is additionally at an isobestic point of the blood absorption spectrum. The next step is to determine the resulting light attenuation LA for each of the three wavelengths w0, w1 and w3:

$$LAw1 = LA(A3w1) + LA(A2w1) - LA(A1w1) - LA(A4w1) \qquad \text{eq. (5)}$$

$$LAw2 = LA(A3w2) + LA(A2w2) - LA(A1w2) - LA(A4w2) \qquad \text{eq. (6)}$$

$$LAw3 = LA(A3w3) + LA(A2w3) - LA(A1w3) - LA(A4w3) \qquad \text{eq. (7)}$$

where LA(Axwy) is the logarithm of received light intensity in the detector related to light arrow Ax at wavelength wy. The suffix x for light arrows Ax represents the number of the selected light arrow and y the suffix for the selected wavelength. Instead of the logarithm of light intensities, light intensity itself can be used in eq. (5)-(7) and "+" is replaced by "*" and "−" is replaced by "/".

In the next step, Rw2,w1 and Rw1,w0 are calculated according to equation (1). As a result R' can be determined using equation (2) with Q as a correction factor which can be dependant on Rw2,w1 or Rw1,w0. The measured arterial oxygenation which is dependant on R' has minimized influence of scattering, blood content or other optical absorbing constituents in tissue.

The quotient in (8) which is part of (2) delivers a measurement variable Rv':

$$Rv' = \frac{LAw2 * LAw0}{LAw1 * LAw1} \qquad \text{eq. (8)}$$

Rv' is a measure of optical absorption of tissue with decreased influence of scattering. Therefore it can be used as a signal for mixed venous oxygenation SvO2.

A mathematically identical form of (2) is:

$$R' = \frac{w2, w0 * Rv' + Q}{Rw1, w0 * Rw1, w0} \qquad \text{eq. (9)}$$

According to eq. (9) the following equation can also be used to determine a measurement variable R1' for SaO2:

$$R1' = \frac{Rw2, w0 * f(1, Rv', Q)}{Rw1, w0 * Rw1, w0} \qquad \text{eq. (10)}$$

where f is an empirical function of optical tissue parameters with variables defined above.

An empirical calibration which reduces influence of absorption and scattering of tissue on the measured variables with the variables LAw1, LAw2, LAw3, Rw1,w2 and Rw2,w3 for the whole saturation range of blood is complex. An pure empirical calibration based on these parameters additionally for different application sites is probably impossible. The proposed model-based method reduces complexity of calibration. SaO2 can be determined with improved accuracy being only dependent on R'.

It is also possible to use this method for other light absorbing constituents of blood like carboxyhemoglobin, methemoglobin, bilirubin or glucose dissolved in blood. Light wavelength in the range from 600 nm-1000 nm can be used for carboxyhemoglobin and methemoglobin. Glucose shows an absorption peek dissolved in blood at 1100 nm and bilirubin in the lower wavelengths range from 300 nm-800 nm. For every additional constituent an additional wavelengths has to be chosen. That means that to measure SaO2 and methemoglobin at a time, four wavelength have to be selected and two different measurement variables R'1 and R'2 according equation (9) have to be defined. Accordingly, the resulting output for SaO2 is dependent on R'1 and methemoglobin on R'2.

As a result sensor 31S is able to measure arterial and mixed venous oxygenation and other blood constituents at a time with reduced influence of measurement errors due to scattering and absorption of tissue.

Example 2

In FIG. 4 finger clip sensor 54 is shown with the two emitters 31E, 32E and the two detectors 31D and 32D. The benefit of the finger clip sensor is that it is easy to apply. Equivalent to sensor 31S in FIG. 3, four representative light paths between the two emitters and the two detectors are possible so that all calculations according example 1 can be performed in order to calculate the output variables R' and Rv' as a measure for mixed venous and arterial oxygenation in the finger 48. The corresponding calculations can also be performed using sensor of FIG. 9. The difference here is the alternative form of detectors 35D and 36D, which are able to increase detected light intensity due to an enlarged, concentric detector area.

Example 3

FIG. 5 shows a multidimensional calibration of SaO2 vs. R1 and R2. R1 and R2 can be calculated according (1) by selecting two wavelengths pairs where for the first wavelengths pair the wavelengths wm1=660 nm and wm2=910 nm is chosen and for the second wavelengths pair wm3=810 nm and wm2=910 nm. The second wavelengths pair is less sensitive towards arterial oxygenation and is used to compensate errors due to optical tissue parameter variations. In order to guarantee that the multidimensional calibration delivers improved precision in presence of varying tissue parameters, it is important to select exactly the correspondent calibration which is specified for a distinct wavelengths set and a distinct detector emitter distance. Therefore additional information has to be coded to the selected sensor. The tissue oximeter device can read out this information and use the appropriate calibration. The coding of information can be achieved for example by a resistor implemented in the LED drive line of the sensor (see FIG. 17: 248, 238). A grounded shield plane 233 between an isolating layer 239 and the light sensing elements 31D an 32D is useful to minimize the electrical interference and noise. The isolating layer can also be used to decouple forces e.g. for wrist worn devices 220 with and integrated sensor interface to control the forces of sensor interface on tissue which can have influences on sensor precision. Also an elastic wrist band 221 can help to decrease this influence.

A variant of a multidimensional calibration (FIG. 5) can be achieved by calculating R1 according to equation (2) and R2 according to equation (8). This minimizes the error of displayed arterial oxygenation SaO2 due to varying optical tissue absorption.

Example 4

In FIG. 7 a fetal pulse oximetry sensor 74 is shown, which punctures the skin on the head of the fetus with a spiral needle 76. The bottom view of FIG. 8 shows sensor 74 with 4 emitters 31E, 32E, 33E, 34E and four detectors 31D, 32D, 33D, 34D. Apparently, more than four different light paths per selected wavelength between emitters and detectors (is) are possible. This additional information is used to calculate a whole set of resulting light attenuations Lax. For the different light paths it is also possible to compute a set of measurement variables Rx. Generating a weighted mean value (weight can depend on the noise of the related measurement signals) LAm and Rm of the variables LAx and Rx helps to reduce errors due to tissue inhomogeneities. To achieve a stable measure for the optical tissue parameters, which are not influenced by locally varying tissue compositions, is important to minimize errors to precisely determine the inputs of model-based parameters.

Example 5

A brain oximeter is shown in FIG. 13A which is positioned on the right side of the forehead of a patient. The cross section of the brain illustrates how four light paths travel through tissue from emitters 31E, 32E to the detectors 31D and 32D, representative for one wavelength. A resulting light attenuation LA can be achieved for each wavelength by adding light attenuations of A32 and A22 and subtracting therefrom the light attentions which are related to A42 and A12. The resulting light attenuation LA is then independent on dirt on emitters or detectors or on degeneration of those parts, which is an important feature since those sensors can be reused. Three wavelengths are chosen for each of the two emitters 31E and 32E of the sensor in FIG. 13A of the brain oximeter: wb1=660 nm, wb2=740 nm and wb3=810 nm.

The ratio Rvb of the resulting light attentions LAwb2 and LAwb3 is used as a measure for the mixed venous oxygenation. The resulting light attenuation at wavelength wb3=810 nm can be used to eliminate the dependency of blood content in tissue of Rvb with a multidimensional calibration of SvO2 vs. Rvb and LAwb3.

A preferred emitter-detector distance between emitter 32E and detector 31D is greater than 2 cm. In order to contrast brain tissue and overlaying tissues one long light path should have an emitter detector distance of about 4 cm and a shorter one with an emitter detector distance of about 2 cm to distinguish the overlaying structures. The relation of noise on the signal and signal portion related mainly to brain is a good compromise for this application. The longer the distance the emitter detector distance is, the deeper is the penetration depth into the brain. In order to achieve maximum penetration depth at a minimum of sensor outline, the distance between an emitter and a detector should be the maximum distance between all emitters and detectors. FIG. 14 shows an example where within the sensor, the two detectors have the maximum distance and the detector and emitter elements are grouped symmetrically with regard to the center of the sensor. The resulting maximum penetration depth of light of A31, A21 is here less than maximum penetration depth of light of A32 of the sensor which illustrated in FIG. 13A because the maximum emitter detector distance is also less compared to sensor in FIG. 13A at the same total outline of the sensors. Positioning emitters and detectors asymmetrically is therefore the best choice to achieve oxygenation measurements in deep layers of tissue. In FIG. 13B emitter 31E is positioned close to emitter 32E. Detector 32D is positioned between detector 31D and emitter 32E. Adding the light attenuation A32 and A22 and subtracting A12 and A42 results in a signal where most of the brain overlaying structures can be contrasted versus brain tissue and where oxygenation signals can be calculated which are originated for more than 80% from brain tissue and not overlaying structures.

FIG. 12 shows a bottom view of a brain oximetry sensor, in which emitter 31E and detectors 31D and 32D are positioned in a triangle. The light paths between emitter 31E and 31D and between 31E and 32D using the wavelengths wb1=660 nm and wb3=810 nm are determined to evaluate the measurement variables Rp1 and Rp2 which are calculated according to equation (1). The mean value of Rp1 and Rp2 is used as the output value for the arterial oxygenation SaO2. Alternatively, as shown in FIG. 12A, the emitters 31E and 32E can be positioned where detectors 31D and 32D are located and detectors 31D and 32D are placed at the location of emitter 31E and 32E in FIG. 12. In FIG. 12B the detector 31D1 is positioned in between of the emitters 31E and 123E. Adding and subtracting light attenuations of the related light paths between 31D1 and 31E and the light path between 31D1 and 123E minimizes the influences of shallow tissue layers as they cancel out. FIG. 12C shows a sensor analogous to FIG. 12B. The difference here is that detector 31D1 is replaced by detector 31D1 and 31D2. Adding the light intensities of this two detectors before calculating the light attenuation thereof results that the related attenuation of detector 31D1 and 31D1 for further calculation can be handled like a single detector. According to this emitters 31E and 123D can be positioned closer by avoiding light shunting between detectors 31D1, 31D2 and emitters 31E and 123E. FIG. 12D shows an alternative position detectors 31D1 and 31D2. In order to monitor the oxygenation balance of brain for both hemispheres a sensor on the right and left side can be used according to the illustration in FIG. 16 with sensor interfaces 214, 215.

Example 6

Referring to Example 5, a brain oximetry sensor was described which is able to determine arterial and mixed venous oxygenation of tissue. These two parameters can be used to calculate the oxygen extraction of tissue. A measure therefore can be the difference of arterial and mixed venous oxygenation. Oxygen extraction reflects how well tissue is supplied with oxygen, and can additionally be used to calculate the cardiac output or the trend of the cardiac output CaOut non-invasively. FIG. 15 shows a patient being supplied with air via an intubation tube 210. The oxygen consumption or CO2 generation is determined within an anesthesia machine 204. Brain oximetry sensor 32S is connected to SaO2 and SvO2 display device 206. The information of device 204 and device 206 is evaluated in a cardiac output monitor 202 in the following or similar manner:

$$CaOut = \frac{(\text{oxygen consumption per time})}{SaO2 - SvO2} \quad \text{eq. (11)}$$

Example 7

Knowledge of oxygenation of tissue of parts of the body is of high interest for sports activity monitoring. The oxygenation the muscles of the upper leg or upper arm can reflect the training level for different activities of sport. FIG. 16 shows an athlete wearing various sensors which are connected by a line or wirelessly with a wrist-worn-display 220. A sports activity sensor can have the same topology as the above mentioned brain sensor of FIG. 12. Emitter-detector distances however vary, depending on desired tissue monitoring depth. Preferred wavelengths to monitor the mixed venous oxygenation are ws1=700 nm, ws2=805 nm and ws3=870 nm. A resulting light attenuation LA is calculated for each wavelength: LWws1, LAws2 and LAws3 with ws1, ws2 and ws3 as index for the selected wavelengths. A measurement variable for the mixed venous oxygenation Rvs is obtained in the following or similar manner:

$$Rvs = \frac{LAws1 - LAws2}{LAws2 - LAws3} \quad \text{eq. (12)}$$

Less influence of light scattering and absorption of tissue can be achieved for the determination of mixed venous oxygenation in this way.

A further improvement for better measurement precision can be achieved by generating an output value for the mixed venous oxygenation which is dependant on a multidimensional calibration of SvO2 vs. Rvs and Rv.

Although the description above contains many specificities, these should not be constructed as limiting the scope of the invention but as merely providing illustrations of some of the presently preferred embodiments of this invention. For example the shape of the emitters can be rectangular, emitters can include LEDs, detectors photodiodes; the shape of the brain sensor can be round; the proposed methods to calculate arterial and mixed venous oxygenation of tissue can be combined in different combinations, signals can be processed by Kalman filters in order to reduce influence of noise caused by motion or other unwanted sources, etc.

The present subject matter includes various examples, including the following:

Example 1 includes an apparatus for measuring tissue oxygenation of a patient comprising:

a sensor interface adapted to be coupled to a patient tissue site and including at least one light emitter emitting light into tissue and at least one detector detecting light passing through tissue from said at least one emitter;

a processor for determining light attenuations LAwsj dependant on light detected at a selected wavelength, wsj;

a coupling device for coupling said sensor interface at said tissue site;

a data processor for generating a signal representative of tissue oxygenation based on said determined light attenuations; and a display device displaying a tissue oxygenation level.

Example 2 includes the apparatus of example 1 wherein said data processor includes means for generating a signal representative of tissue oxygenation and provides arterial oxygenation information based on pulsating changes of light attenuations.

Example 3 includes the apparatus of example 2 wherein said sensor coupling device is an arm band.

Example 4 includes the apparatus of example 3 wherein said armband is a wrist band.

Example 5 includes the apparatus of example 3 comprising: elastic means for controlling a force applied to tissue through the sensor interface.

Example 6 includes an apparatus for measuring tissue oxygenation comprising:

a sensor interface including at least two emitters which emits light into tissue with at least two wavelengths, and at least one detector to receive light passing through said tissue;

a storage device for retaining information of sensor variation within said sensor interface; and a processor for determining tissue oxygenation using said sensor variation information of said sensor interface.

Example 7 includes the apparatus according to example 6 wherein a light emission intensity of at least one of said emitters and a wavelength of at least one of said emitters is compensated for by said means for calculating.

Example 8 includes the apparatus according to example 7 wherein brain tissue oxygenation is determined using said sensor interface with at least one emitter/detector distance being greater than 3 cm and said sensor interface being provided at one side of a forehead, said apparatus measuring the oxygenation of one brain hemisphere.

Example 9 includes the apparatus according to example 8 wherein at least one emitter detector distance is about 1 cm long and a related path can be used to determine a light attenuation or additionally arterial oxygenation by evaluating a pulsatile part of detected light.

Example 10 includes an apparatus for measuring tissue oxygenation comprising:

a sensor adapted to be coupled to a forehead tissue including at least two light emitters placed apart from each other on said sensor with at least two different wavelengths for each emitter where each emitter has approximately the same wavelengths which emit light into said tissue and at least one detector for detecting light having passed through said tissue, whereby a distance of one of said emitters and one of said at least one detector is chosen so that a light path penetrates through the tissue and whereby a distance between at least one emitter-detector pair is more than 20 millimeters;

means for calculating at least two signals which depend on detected light for selected wavelengths wsj for said at least one detector and said at least two emitters, wherein said at least two signals are calculated by adding or subtracting light attenuations;

means for calculating attenuation corresponding to ln(intensity of steady state light received at the detector) for at least two possible light paths between said at least two light emitters and said at least one detector; and means for generating an output representative of tissue oxygenation based on the at least said two signals.

Example 11 includes the apparatus of example 10 using at least two emitters and at least two detectors whereby for at least two of said wavelengths for each of the wavelengths the corresponding light attenuations for two light paths are added and the corresponding light attenuation for two further light paths are subtracted to generate a measure for said at least two signals.

Example 12 includes the apparatus of example 11 wherein said sensor includes at least one emitter detector distance of at least 4 cm and a second emitter detector distance of at least 1.5 cm.

Example 13 includes the apparatus of example 10 wherein said sensor includes at least one emitter detector distance of at least 4 cm and a second emitter detector distance of at least 1.5 cm.

Example 14 includes the apparatus of example 12 wherein at least 65% of a generated oxygenation signal is originated by brain tissue by adding and subtracting light paths through forehead tissue and brain tissue.

Example 15 includes the apparatus of example 13 wherein an emitter-detector distance of the sensor placed on one side of the forehead to monitor a brain hemisphere is less than 20 mm long.

Example 16 includes the apparatus of example 13 having a means to calculate a measure for arterial oxygenation using a light signal related to an emitter-detector pair separated by a distance of no more than 20 mm.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An apparatus for measuring oxygenation comprising:
    a sensor interface having a surface and including at least one emitter on the surface, the emitter configured to emit light of at least two wavelengths into tissue proximate the surface, and including at least two detectors including a first detector and a second detector, wherein the first detector is configured to generate a first output signal corresponding to detected light of the at least two wavelengths passing through the tissue along a first plurality of paths and wherein the second detector is configured to generate a second output signal corresponding to detected light of the at least two wavelengths passing through the tissue along a second plurality of paths, wherein at least one path is configured to provide a depth of penetration of a light path that travels in a selected region of the tissue;
    a storage device within the sensor interface for retaining information corresponding to calibration, the retained information based on the emitter and detectors configuration and based on the at least two wavelengths, wherein the retained information is determined by a distance between the at least one emitter and a detector; and
    a processor configured to determine oxygenation corresponding to oxygenated venous blood at the selected region of the tissue, the oxygenation determined based on the first output signal, the second output signal, and the retained information, wherein the oxygenation is determined based on a difference of light attenuations at each wavelength of the at least two wavelengths.

2. The apparatus of claim 1 wherein a distance between at least one emitter and at least one detector is at least 4 cm.

3. The apparatus of claim 1 wherein a distance between at least one emitter and at least one detector is about 1 cm.

4. The apparatus of claim 1 wherein the processor is configured to determine oxygenation using an empirical calibration.

5. The apparatus of claim 1 wherein the processor is configured to implement a model-based calculation, wherein the model-based calculation is configured to reduce influence of measurement error due to scattering.

6. The apparatus of claim 1 wherein the processor is configured to perform a calculation including determining an addition of two light attenuations and determining a subtraction of two light attenuations, the light attenuations corresponding to light along the plurality of paths.

7. The apparatus of claim 6 wherein the processor is configured to perform the calculation for a plurality of wavelengths.

8. The apparatus of claim 1 wherein the information is determined by a wavelength.

9. The apparatus of claim 1 wherein the information includes a resistor value.

10. The apparatus of claim 1 wherein the information includes a value corresponding to brain tissue.

11. The apparatus of claim 1 wherein the sensor interface is configured for attachment to a forehead.

12. An apparatus for measuring oxygenation comprising:
    a sensor interface having a surface and including at least one emitter on the surface, the emitter configured to emit light of at least two wavelengths into tissue proximate the surface, and including at least two detectors including a first detector and a second detector, wherein the first detector is configured to generate a first output signal corresponding to detected light of the at least two wavelengths passing through the tissue along a first plurality of light paths and wherein the second detector is configured to generate a second output signal corresponding to detected light of the at least two wavelengths passing through the tissue along a second plurality of light paths, wherein at least one light path is configured to provide a depth of penetration of a light path that travels in a selected region of the tissue;
    coding hardware configured to store sensor interface information, the sensor interface information based on the emitter and detectors configuration and based on the at least two wavelengths, wherein the sensor interface information is determined by a distance between the at least one emitter and a detector; and
    a processor coupled to the sensor interface and coupled to the coding hardware, the processor configured to determine oxygenation corresponding to oxygenated venous blood at the selected region of the tissue, the oxygenation determined based on the sensor interface information, the first output signal, the second output signal, a difference of light attenuations at each wavelength of the at least two wavelengths, and a model-based calculation, the model-based calculation corresponding to decreased scattering as a function of wavelength.

13. The apparatus of claim 12 wherein the at least two emitters includes a first emitter, a second emitter, and a third emitter.

14. The apparatus of claim 13 wherein the first emitter has a first wavelength, the second emitter has a second wavelength, and the third emitter has a third wavelength, and further wherein the third wavelength is about a geometric mean value of the first wavelength and the second wavelength.

15. The apparatus of claim 12 wherein the processor is configured to perform a calculation including determining an addition of two light attenuations and determining a subtraction of two light attenuations, the light attenuations corresponding to light along the plurality of light paths.

16. The apparatus of claim 15 wherein the processor is configured to perform the calculation for a plurality of wavelengths.

17. The apparatus of claim 12 further including a circuit coupled to the sensor interface, the circuit configured to generate the model-based calculation.

18. A method of determining tissue oxygenation comprising:

positioning at least one emitter and a plurality of detectors on a surface of a sensor interface, the at least one emitter configured to emit light having a plurality of wavelengths into tissue proximate the surface and each of the plurality of detectors configured to provide an output signal corresponding to light detected by the detector, wherein at least one detector is configured to provide an output signal corresponding to a light path through a selected region of the tissue, the selected region corresponding to a depth of penetration and the depth of penetration corresponding to a distance between the emitter and the plurality of detectors;

coupling coding hardware to the sensor interface, the coding hardware configured to store sensor interface information, the sensor interface information based on the emitter and detectors configuration and based on the at least two wavelengths, wherein the sensor interface information is determined by a distance between the at least one emitter and a detector; and configuring a processor to calculate oxygenation corresponding to oxygenated venous blood at the selected region of the tissue, the oxygenation determined based on the sensor interface information, the output signals, a difference of light attenuations at each wavelength of the at least two wavelengths, and a model-based calculation, the model-based calculation corresponding to decreased scattering as a function of wavelength.

19. The method of claim 18 wherein positioning includes establishing the distance at 2 cm.

20. The method of claim 18 wherein positioning includes establishing the distance at 4 cm.

21. The method of claim 18 further including configuring the sensor interface to couple with tissue proximate a human brain.

22. The method of claim 18 wherein positioning includes positioning a first emitter, a second emitter, and a third emitter.

23. The method of claim 22 further including selecting the first emitter, the second emitter, and the third emitter wherein the first emitter has a first wavelength, the second emitter has a second wavelength, and the third emitter has a third wavelength, and further wherein the third wavelength is about a geometric mean value of the first wavelength and the second wavelength.

24. The method of claim 18 further including storing sensor interface information in the coding hardware and wherein storing includes selecting a resistor value.

* * * * *